(12) United States Patent
Uhrich et al.

(10) Patent No.: US 9,618,470 B2
(45) Date of Patent: Apr. 11, 2017

(54) HUMIDITY SENSOR AND ENGINE SYSTEM

(71) Applicant: Ford Global Technologies, LLC, Dearborn, MI (US)

(72) Inventors: Michael James Uhrich, West Bloomfield, MI (US); Yong-Wha Kim, Ann Arbor, MI (US); Ross Dykstra Pursifull, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 800 days.

(21) Appl. No.: 13/865,877

(22) Filed: Apr. 18, 2013

(65) Prior Publication Data
US 2014/0316672 A1    Oct. 23, 2014

(51) Int. Cl.
| | | |
|---|---|---|
| G01N 27/22 | (2006.01) |
| F02P 5/04 | (2006.01) |
| G01N 27/14 | (2006.01) |
| F02P 5/152 | (2006.01) |

(52) U.S. Cl.
CPC ............ *G01N 27/223* (2013.01); *F02P 5/045* (2013.01); *F02P 5/152* (2013.01); *G01N 27/14* (2013.01)

(58) Field of Classification Search
CPC ........... F02D 2200/0418; F02D 41/222; F02D 41/005; F02D 2200/0414; F02D 41/0065; F02D 41/0245; F02D 41/064
USPC ........................................ 123/568.11–568.32
See application file for complete search history.

(56) References Cited

U.S. PATENT DOCUMENTS

| | | | | |
|---|---|---|---|---|
| 6,073,480 A * | 6/2000 | Gokhfeld | ............ | G01N 27/124 73/29.02 |
| 8,726,658 B2 * | 5/2014 | Styles | ..................... | F02B 37/12 123/562 |
| 8,746,217 B2 * | 6/2014 | Piper | ..................... | F02B 37/004 123/568.12 |
| 8,881,713 B2 * | 11/2014 | Surnilla | .............. | F02D 41/0245 123/568.22 |
| 2012/0227714 A1 | 9/2012 | Surnilla et al. | | |
| 2014/0316676 A1 * | 10/2014 | Pursifull | ................. | F02P 5/045 701/103 |

FOREIGN PATENT DOCUMENTS

WO    WO 2011138387 A1 * 11/2011

OTHER PUBLICATIONS

Pursifull, Ross Dykstra, "Humidity Sensor Diagnostics," U.S. Appl. No. 13/774,282, filed Feb. 22, 2013, 48 pages.
Pursifull, Ross Dykstra, "Humidity Sensor Diagnostics," U.S. Appl. No. 13/774,319, filed Feb. 22, 2013, 46 pages.
Pursifull, Ross Dykstra, "Humidity Sensor Diagnostic Method Using Condensation Clearing Heater," U.S. Appl. No. 13/857,884, filed Apr. 5, 2013, 38 pages.
Pursifull, Ross Dykstra, "Humidity Sensor and Engine System," U.S. Appl. No. 13/865,853, filed Apr. 18, 2013, 34 pages.

* cited by examiner

*Primary Examiner* — Sizo Vilakazi
(74) *Attorney, Agent, or Firm* — Julia Voutyras; McCoy Russell LLP (57) ABSTRACT

Methods and systems are provided for an engine coupled temperature-based humidity sensor. Degradation of the humidity sensor may be determined while flowing gasses into an engine intake air downstream of a humidity sensor and upstream of a compressor, indicating humidity sensor degradation when relative humidity readings change by less (Continued)

than a threshold while temperature at the sensor changes greater than a second threshold.

20 Claims, 8 Drawing Sheets

HUMIDITY SENSOR AND ENGINE SYSTEM

BACKGROUND AND SUMMARY

Engines may utilize humidity sensors at various locations for controlling engine operation, such as for controlling spark timing and exhaust gas recirculation (EGR). Errors in the humidity reading can lead to improper spark timing, and thus knock, as well as various other issues with regard to condensate formation, EGR control, diluent control, etc.

US 20120227714 describes an approach with a humidity sensor positioned downstream of an EGR inlet. To diagnose operation of the sensor, the disclosed method closes the EGR throttle valve, and indicates humidity sensor degradation based on each of a change in intake air relative humidity and pressure responsive to the EGR throttle valve closing.

The Inventors have recognized a problem with monitoring humidity sensors based on a reading difference under a change in absolute pressure when specific or absolute humidity is low (e.g. relatively dry air). Under such conditions, humidity readings result in a lack of noticeable relative humidity change. In one example, the engine may be diagnosed by a method comprising: while flowing gasses into an engine intake air downstream of a humidity sensor and upstream of a compressor, indicating humidity sensor degradation when relative humidity readings change by less than a threshold while temperature at the sensor change greater than a second threshold.

For example, where the sensor is a temperature-based humidity sensor and/or relative humidity sensor, under low specific and relative humidity conditions, the temperature sensor is sensitive to natural temperature rise over ambient air. Thus, a correlation exists such that an increase in ambient air temperature changes relative humidity if specific humidity is kept constant. Therefore, by monitoring relative humidity changes while the sampled air temperature changes, it is possible to identify whether the sensor is functioning, including whether underhood temperatures change relative humidity as expected, and from that identify sensor degradation.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The following description relates to systems and methods for diagnosing a humidity sensor, and taking default operation in response thereto.

One issue is that certain humidity sensor technologies positioned to measure engine inlet air humidity becomes difficult to diagnose because its measurement experiences little change in response to a pressure or a temperature change. It could readily appear to be "stuck in range." As such, a specific humidity sensor is insensitive to pressure and temperature changes if specific humidity remains constant. However, when specific humidity remains constant, absolute humidity sensors are sensitive to pressure and temperature changes when the ambient air is hot and humid. When the ambient air is dry, absolute humidity sensors have very little sensitivity to pressure and temperature changes. Further, when specific humidity is constant, relative humidity sensors are sensitive to pressure and temperature changes even when the ambient air becomes dry. As explained further herein, by varying the pressure of intake air to be sampled in the proximity of the three-way humidity sensor, while avoiding other contaminating engine flows, it is possible to correlate a change in specific humidity to the varying pressure. Further, it is possible to correlate a change in relative humidity with temperature change. When the correlations are not identified, degradation of the sensor may be indicated and default operation enacted.

Specifically, the change in the absolute humidity is related to the change in total pressure. In other words, if the total pressure of an air/water mixture is reduced by 10%, than the absolute humidity is reduced by approximately 10%. By changing the inlet air pressure relatively slowly with respect to engine operation transients, but faster than steady state operation, it is possible to verify whether a relatively slowly changing ratio between water and the air/water mixture is not changing as the mixture is compressed or expanded. Further, specific humidity is expressed as a ratio of mass of water vapor per unit mass of dry air (e.g. humidity ratio). In one specific example, a humidity sensor positioned downstream of a pre-compressor throttle provides improved sensitivity because at this point potential humidification from crankcase gasses or circulated exhaust are not yet added.

In one example, the humidity sensor is a capacitance-based humidity sensor. The capacitance sensor is primarily sensitive to absolute humidity. Specifically, it is sensitive to the amount of water in a given volume (between the capacitor's plates). If one lowers the total pressure, the capacitance is reduced. In some examples, the present approach takes advantage of this relationship, noting that absolute humidity is directly proportional to density, absolute humidity is directly proportional to pressure—at constant temperature, and absolute humidity is inversely proportional to temperature—at constant pressure.

As described herein, by varying the pressure of a sample air/water mixture and reading the absolute humidity of the sensor, humidity sensor performance can be assessed. The absolute humidity directly varies with the total pressure of the mixture, and so the sensor is substantially an absolute humidity sensor, where pressure is directly proportional to absolute humidity. Thus, when the upstream air intake throttle is closed and the pressure lowered from 100 kPa to 90 kPa, the absolute humidity can be expected to decrease by 10% (plus/minus a tolerance threshold) when the sensor is functioning properly. Such an approach can be contrasted with one aiming to convert the absolute humidity to a relative humidity.

As used herein, the following apply:

Humidity ratio=Specific Humidity=water mass/dry air mass

Absolute humidity=mass of water in a given volume of air–water mixture

Relative Humidity=mole fraction of water in mixture/mole fraction of water in saturated mixture.

Figure 1:
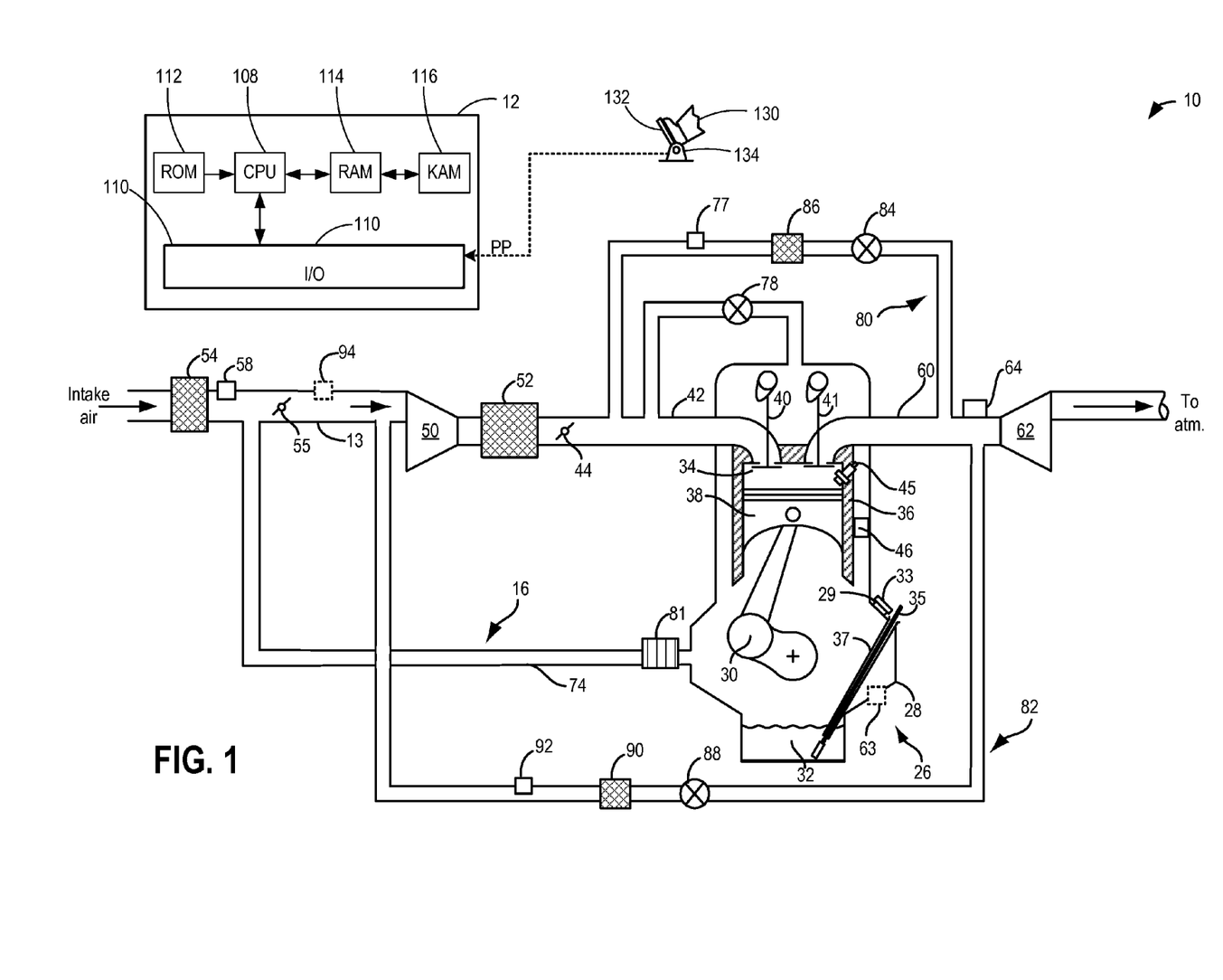
FIG. 1 shows an engine system including a humidity sensor
Figure 3:
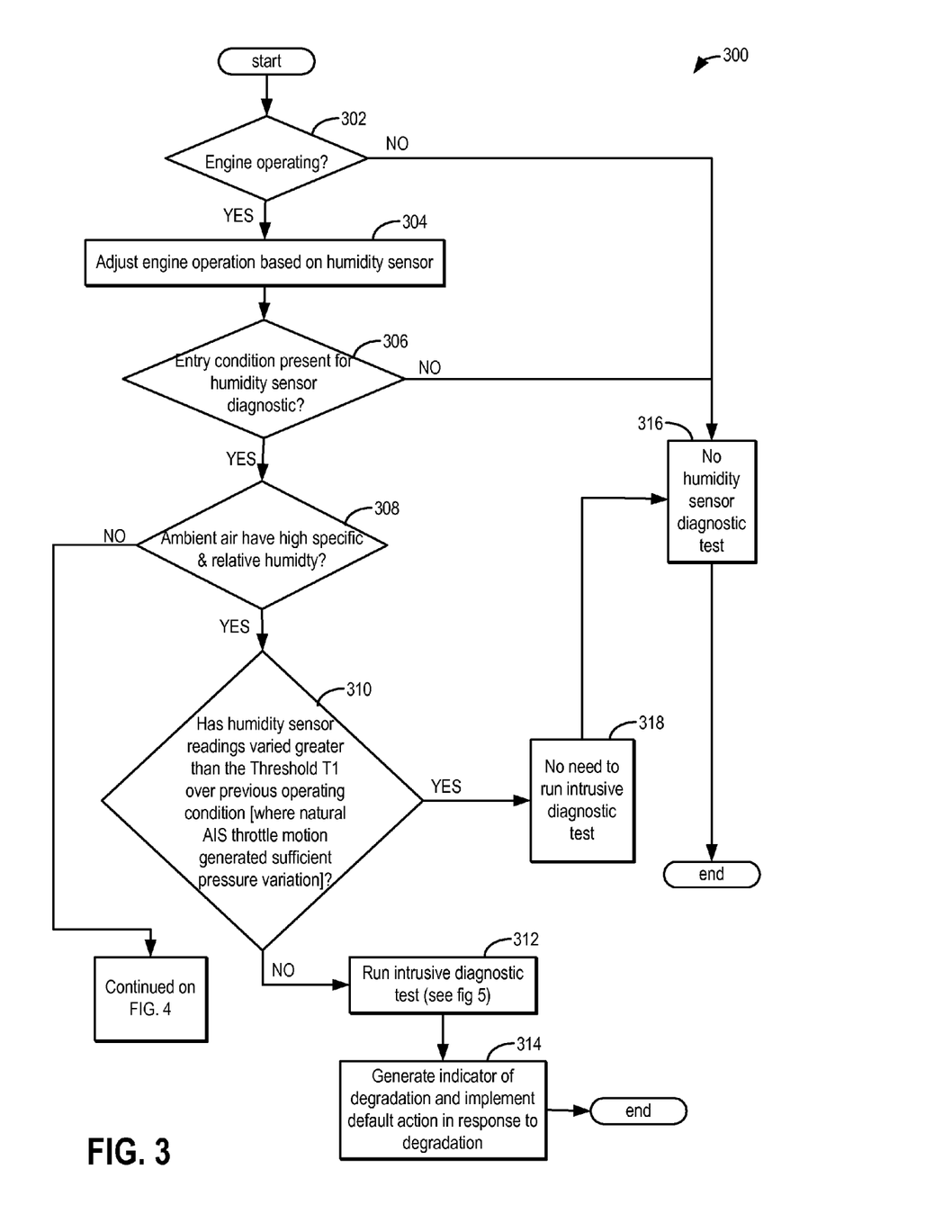
FIG. 3 shows a flow chart of a method for diagnosing a capacitance-based humidity sensor based on high specific and relative humidity conditions
Figure 4:
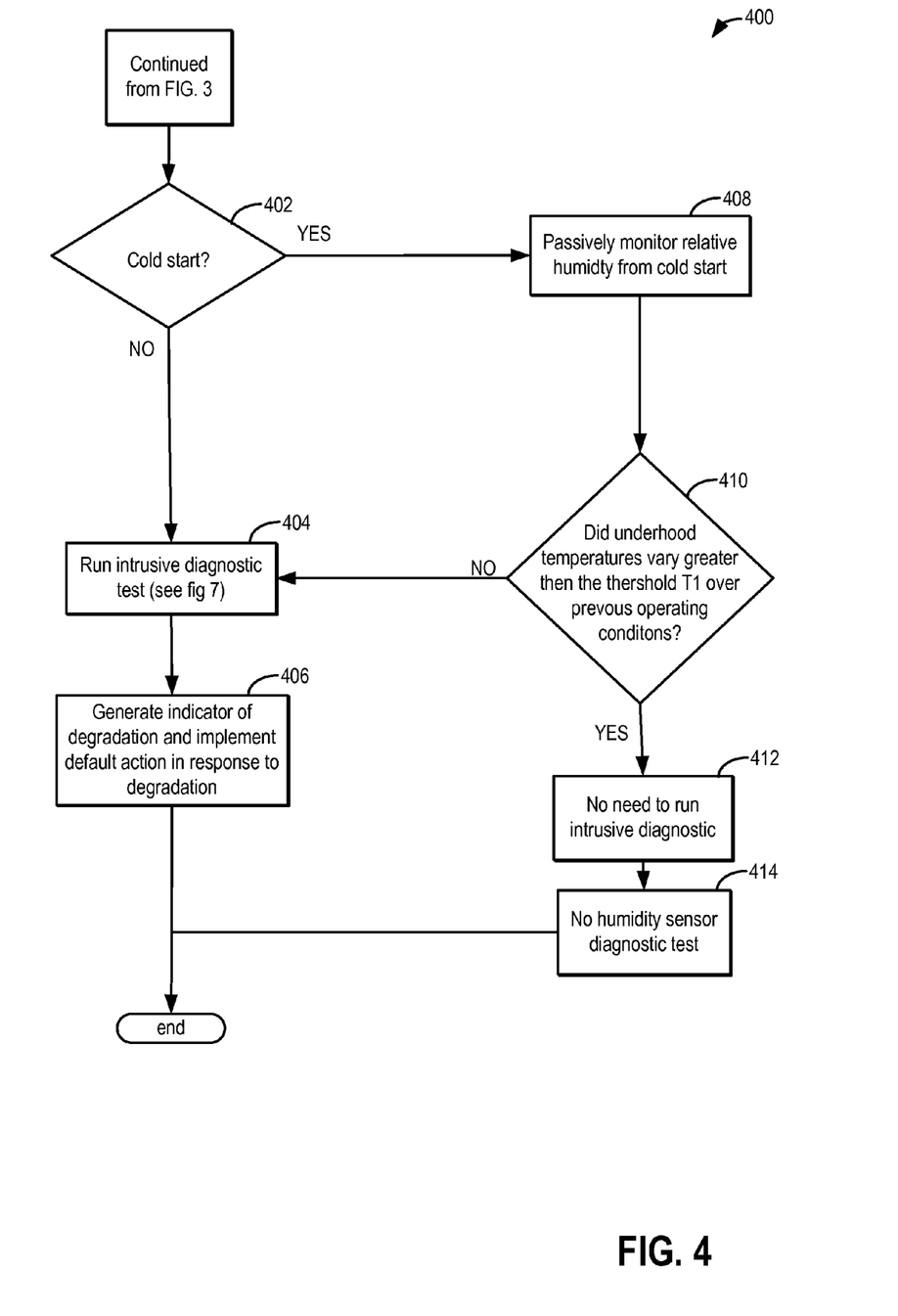
FIG. 4 shows a flow chart of a method for diagnosing a temperature-based humidity sensor based on low specific and relative humidity conditions

The following description relates to systems and methods for diagnosing a humidity sensor coupled in an engine system having an intake system with a compressor (FIG. 1). A humidity sensor, such as a capacitance-based humidity sensor, may be positioned downstream of a pre-compressor throttle to measure or estimate humidity under different engine operating conditions. The capacitance-based humidity sensor (FIG. 2) is primarily sensitive to absolute humidity; therefore, if one varies the pressure of an air/water mixture and reads absolute humidity, the humidity sensor can be assessed. Specifically, the humidity sensor may be periodically diagnosed based on current engine conditions (FIGS. 3 and 4). Further, an intrusive humidity sensor diagnostic test, based on absolute humidity (FIG. 5) or temperature (FIG. 7), is run if the engine's natural variation and operation does not cause the humidity sensor reading to vary over a threshold range indicating degradation of the humidity sensor. Example humidity sensor readings based on engine operating conditions are shown at FIGS. 6 and 8.

Referring now to FIG. 1, it shows an example system configuration of a multi-cylinder engine, generally depicted at 10, which may be included in a propulsion system of an automobile. Engine 10 may be controlled at least partially by a control system including engine controller 12 and by input from a vehicle operator 130 via an input device 132. In this example, input device 132 includes an accelerator pedal and a pedal position sensor 134 for generating a proportional pedal position signal PP.

Engine 10 may include a lower portion of the engine block, indicated generally at 26, which may include a crankcase 28 encasing a crankshaft 30 with oil well 32 positioned below the crankshaft. An oil fill port 29 may be disposed in crankcase 28 so that oil may be supplied to oil well 32. Oil fill port 29 may include an oil cap 33 to seal oil fill port 29 when the engine is in operation. A dip stick tube 37 may also be disposed in crankcase 28 and may include a dipstick 35 for measuring a level of oil in oil well 32. In addition, crankcase 28 may include a plurality of other orifices for servicing components in crankcase 28. These orifices in crankcase 28 may be maintained closed during engine operation so that a crankcase ventilation system (described below) may operate during engine operation.

The upper portion of engine block 26 may include a combustion chamber (e.g., cylinder) 34. The combustion chamber 34 may include combustion chamber walls 36 with piston 38 positioned therein. Piston 38 may be coupled to crankshaft 30 so that reciprocating motion of the piston is translated into rotational motion of the crankshaft. Combustion chamber 34 may receive fuel from fuel injector 45 (configured herein as a direct fuel injector) and intake air from intake manifold 42 which is positioned downstream of throttle 44. The engine block 26 may also include an engine coolant temperature (ECT) sensor 46 input into an engine controller 12 (described in more detail below herein).

A throttle 44 may be disposed in the engine intake to control the airflow entering intake manifold 42 and may be preceded upstream by compressor 50 followed by charge air cooler 52, for example. An air filter 54 may be positioned upstream compressor 50 and may filter fresh air entering intake passage 13. The intake air may enter combustion chamber 34 via cam-actuated intake valve system 40. Likewise, combusted exhaust gas may exit combustion chamber 34 via cam-actuated exhaust valve system 41. In an alternate embodiment, one or more of the intake valve system and the exhaust valve system may be electrically actuated.

Exhaust combustion gases exit the combustion chamber 34 via exhaust passage 60 located upstream of turbine 62. An exhaust gas sensor 64 may be disposed along exhaust passage 60 upstream of turbine 62. Turbine 62 may be equipped with a wastegate bypassing it. Exhaust gas sensor 64 may be a suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a NOx, HC, or CO sensor. Exhaust gas sensor 64 may be connected with engine controller 12.

In the example of FIG. 1 a crankcase ventilation tube 74 is coupled to the engine intake so that gasses in the crankcase may be vented in a controlled manner from the crankcase. During non-boosted conditions (when manifold pressure (MAP) is less than compressor inlet pressure (CIP)), the crankcase ventilation system 16 draws air into crankcase 28 via a breather or ventilation tube 74. Crankcase ventilation tube 74 may be coupled to fresh air intake passage 13 upstream of compressor 50. In some examples, crankcase vent tube may be coupled downstream of air filter 54 (as shown). In other examples, crankcase ventilation tube may be coupled to intake passage 13 upstream of air filter 54.

The crankcase gases may include blow-by of combustion gases from the combustion chamber to the crankcase. The composition of the gases flowing through the conduit, including the humidity level of the gasses, may affect the humidity at locations downstream of the PCV inlet in the intake system.

Gas may flow through crankcase ventilation tube 74 in both directions, from crankcase 28 towards intake passage 13 and/or from intake passage 13 towards crankcase 28. For example, during non-boosted conditions where MAP is lower than CIP, air flows through ventilation tube 74 from intake passage 13 to crankcase 28. In comparison, during boosted engine operation (when MAP is higher than CIP), crankcase vapors may flow through ventilation tube 74 from crankcase 28 to intake passage 13. Further, oil separator 81 may be disposed in ventilation tube 74 to remove oil from the stream of gasses exiting the crankcases during boosted operation.

A low pressure exhaust gas recirculation (LP-EGR) system may route a desired portion of exhaust gas from exhaust passage 60 to intake passage 13 via LP-EGR passage 82. The amount of LP-EGR provided to intake passage 13 may be varied by engine controller 12 via EGR valve 88. Further, followed by air cooler 90, an LP-EGR sensor 92 may be arranged within the LP-EGR passage and may provide an indication of one or more pressure, temperature, and concentration of the exhaust gas. In some examples, LP-EGR sensor 92 may provide one indication of an amount of LP-EGR. The EGR amount may alternatively, or additionally, be determined from humidity readings and other operating parameters, as described in detail below. A high pressure EGR (HP-EGR) system may route a desired portion of exhaust gas from exhaust passage 60 to intake passage 13 via HP-EGR passage 80. The amount of HP-EGR provided to intake passage 13 may be varied by engine controller 12 via EGR valve 84. Further, followed by air cooler 86, an HP-EGR sensor 77 may be arranged within the HP-EGR passage and may provide an indication of one or more pressure, temperature, and concentration of the exhaust gas.

Under some conditions, the EGR system may be used to regulate the temperature of the air and fuel mixture within the combustion chamber, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

It will be appreciated that, as used herein, PCV flow refers to the flow of gases through the PCV line. This flow of gases may include a flow of intake air only, a flow of crankcase gases only, and/or a flow of a mixture of air and crankcase gases, the composition of the flow based at least on the direction of the flow as well as MAP conditions relative to CIP at the time of flow.

Engine controller 12 is shown in FIG. 1 as a microcomputer, including microprocessor unit 108, input/output ports 110, an electronic storage medium for executable programs and calibration values shown as read only memory chip 112 in this particular example, random access memory 114, keep alive memory 116, and a data bus. Engine controller 12 may receive various signals from sensors coupled to engine 10, including measurement of inducted mass air flow (MAF) from mass air flow sensor 58; engine coolant temperature (ECT) from temperature sensor 46; exhaust gas air/fuel ratio from exhaust gas sensor 64; etc. Furthermore, engine controller 12 may monitor and adjust the position of various actuators based on input received from the various sensors. These actuators may include, for example, throttle 44, intake and exhaust valve system 40, 41, and PCV valve 78. Storage medium read-only memory 112 can be programmed with computer readable data representing instructions executable by processor 108 for performing the methods described below, as well as other variants that are anticipated but not specifically listed thereof.

A humidity sensor 94 is positioned upstream of a compressor, in between the LP-EGR 82 inlet and ventilation system 16 inlets, and downstream of mass air flow sensor 58 and pre-compressor throttle 55 in an engine intake system. In this position, the humidity sensor is able to measure air/water mixture to report absolute humidity such that a change in absolute humidity directly varies with the total pressure of the air/water mixture. For example, if the total pressure of air/water mixture is reduced by 10% than the absolute humidity is reduced by 10%. Additional details of an example humidity sensor 94 are described further with regard to FIG. 2.

Figure 2:
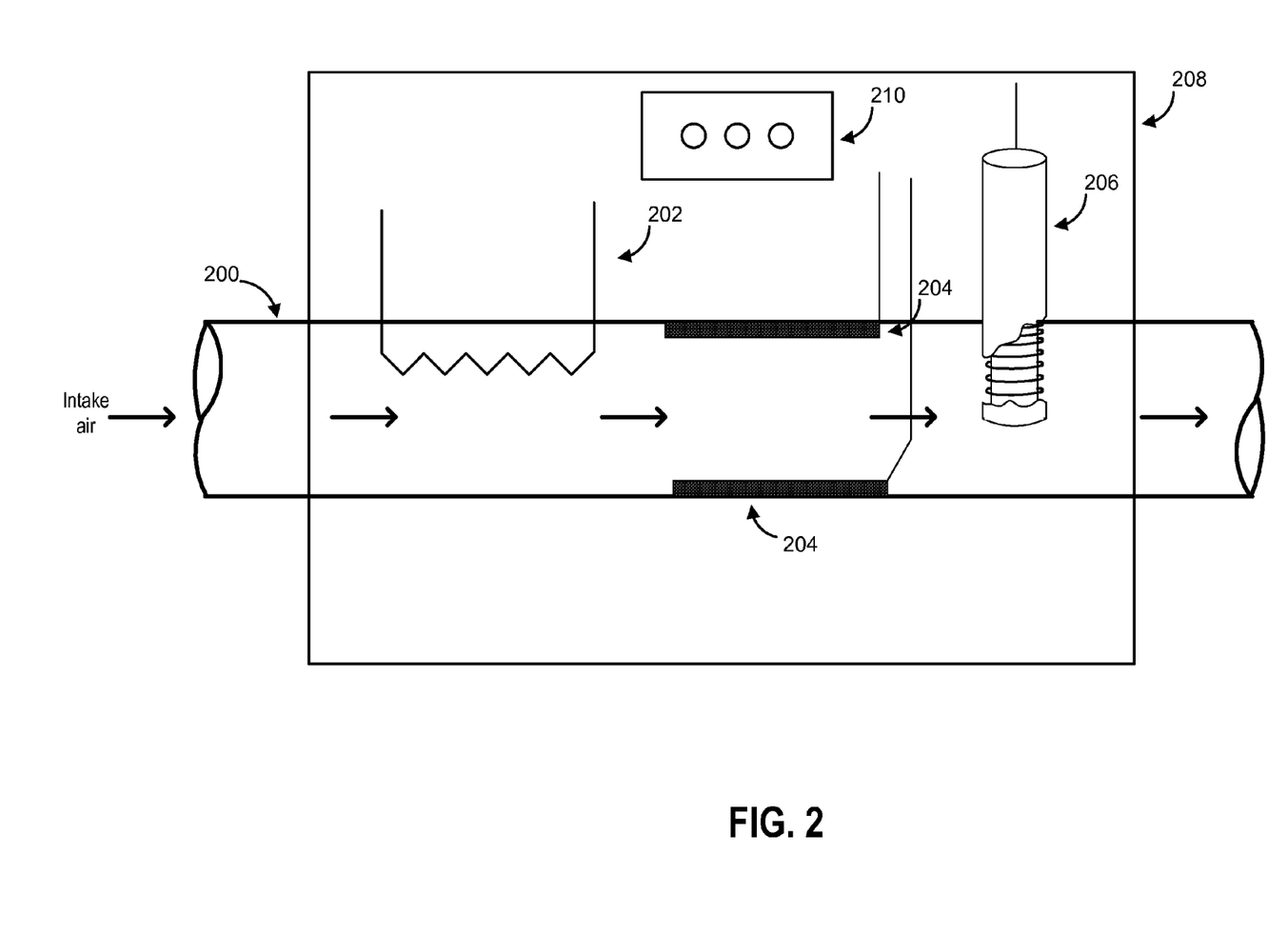
FIG. 2 shows a schematic embodiment of a capacitance-based humidity sensor

FIG. 2 is a schematic depiction of an embodiment of a capacitance-based humidity sensor including a temperature sensor, a capacitance sensor, and a condensation heater. Sample air may flow through a passage 200, which may be a passage upstream of compressor 50, for example. The humidity sensor disclosed may couple a heater 202, a pair of parallel capacitive plates 204, and a temperature sensor 206 positioned along intake air flow. The depicted temperature sensor 206 is a coiled resistance thermometer; however, other embodiments may use other temperature sensors such as alternate resistance thermometer configurations or a thermocouple. The heater 202 depicted is a resistive heater; other embodiments may similarly use other heaters. The heater 202, capacitor 204, and temperature sensor 206 may be aligned linearly such the intake air flowing past the heater may pass through the capacitor and thermally interact with the temperature sensor. Further, the heater 202, capacitor 204, and temperature sensor 206 may be contained in a common sensor housing 208, and include signal conditioning electronics 210 in order to communicate with the engine controller 12 of FIG. 1 that has memory with non-transitory instructions to indicate humidity sensor degradation.

When activated by the engine controller, heater 202 may increase the local temperature within the humidity sensor. The increased local temperature may cause the aircharge within the humidity sensor, between the parallel plates of the capacitor 204 specifically, to expand. Because this expansion is homogenous, the amount of water vapor within the volume between the parallel plates may decrease causing an increase in capacitance. Temperature sensor 206 may then measure the temperature of the air that has traversed the capacitor in order to provide a corrected humidity sensor reading. In one example, the sensor may provide absolute, relative, or other humidity measurements of engine intake.

Now turning to FIG. 3, the method shows how an intrusive humidity sensor diagnostic test is performed if the engine's natural variation and operation does not cause the humidity sensor reading to sufficiently vary over a threshold range (see also FIG. 6 graphs). For example, an engine in a vehicle can have widely varying airflow and pressure depending on the operating conditions of the vehicle. Under some driving scenarios, the pressure variation is enough to cause the humidity reading to fluctuate sufficiently to estimate that it is working properly. One such example is that the natural pre-compressor throttle motion generates sufficient pressure variation greater than threshold. However, under other conditions, the humidity sensor may not experience sufficient pressure variations and so engine operation, including pre-compressor throttle operation, may be modified to enable diagnostic monitoring of the humidity sensor during engine operation.

Method 300 begins at 302 by analyzing engine operating conditions. Engine operating conditions may include engine speed and load, MAP, humidity (e.g. sensed humidity measured from humidity sensor 94), air mass flow, barometric pressure (BP), etc. If the engine is not operating, the humidity sensor may not be able to measure generated pressure variation greater than threshold. Thus, at 304, no humidity sensor diagnostic test is made, and no indication and/or default action is carried out.

Returning to 302, if the engine is operating, the routine continues to 303 to adjust engine operation responsive to humidity sensor readings. For example, the routine may adjust spark timing based on humidity, including advancing ignition timing for a given speed and load condition at higher humidity values, and retarding the ignition timing at lower humidity values. Next, at 308, the routine determines if the entry conditions are present for the humidity sensor diagnostic test. Entry conditions may include engine operating at steady conditions (e.g., RPM fluctuation less than 50 RPM over 1 second), temperature warmed up past threshold operating temperature, boost, ambient temperature within a threshold, temperature changes within a range. If appropriate entry conditions are not present, at 306, no humidity sensor diagnostic test is made (316). Returning to 306, if the entry conditions are present for the humidity sensor diagnostic, the routine continues to 308 to determine if the ambient air has high specific and relative humidity (e.g. the ambient air is hot and humid). In one example, changes in relative humidity can be observed when ambient conditions have high specific and relative humidity with an increase in pressure. Therefore, at 310, if high specific and relative humidity are present, the routine determines if the humidity sensor readings have varied greater than the threshold T1 over previous operating conditions. For example, the routine can compare a current reading at the current operating conditions to previous readings at previous operating conditions to identify whether over a duration, a sufficient variation of the humidity sensor reading greater than a threshold is present. Natural change in compressor inlet pressure, for example, may be generated when a change in the AIS throttle position is commanded to maintain or provide a desired low pressure EGR flow rate. If the humidity sensor readings do not vary sufficiently, degradation of the sensor is possible; therefore, an intrusive diagnostic test is run at 312 (see also FIG. 5). However, at 310, if the humidity sensor readings vary greater than the threshold (T1), then the intrusive diagnostic test (318) and a humidity sensor diagnostic test (316) are not run.

At 312, an intrusive adjustment of engine operation may be performed in order to improve observability of humidity sensor performance and thus enable humidity sensor diagnostics. In one example, the intrusive adjustment may include periodic, or cyclical, adjustment of the pre-compressor throttle to generate pressure variations at the humidity sensor, which then generates corresponding humidity sensor reading changes as described herein. The degree of variation of the pre-compressor throttle may be selected based on current operating conditions, such as a current boost level, and a degree to which the boost level is above ambient pressure. The degree of variation of the pre-compressor throttle may be selected based on a desired span of pressure changes at the humidity sensor for the intrusive diagnostic. For example, by adjusting the pre-compressor throttle across a range of throttle angles, during engine operating conditions, the sensor may be sensitive to the variations in pressure when functioning properly, and thus variation in the humidity sensor reading that correlates with the pressure change may be used to determine proper sensor functionality. In another example, intrusive pressure changes may be generated by adjusting a commanded compressor inlet pressure responsive to the routine reaching block 312. Closed loop control of compressor inlet pressure, e.g., via adjustment of the pre-compressor throttle and feedback from a compressor inlet pressure sensor, can therefore provide intrusive adjustment of pressure at the humidity sensor.

Additionally, or alternatively, the frequency of pre-compressor throttle variation, and/or pressure variation at the humidity sensor may be correlated to the frequency of humidity sensor reading variation. For example, if a frequency of oscillations of the pre-compressor throttle is within a threshold range of a resulting frequency of humidity sensor variations, then proper sensor functionality may be indicated, and if not, sensor degradation indicated.

In this way, an indication of degradation of the humidity sensor may be generated when humidity sensor readings change by less than a first threshold while pressure at the sensor changes greater then a second threshold. Additionally, or alternatively, the indication of degradation of the humidity sensor may be generated when a frequency of humidity sensor readings differs by more than a threshold from a frequency of pressure variations at the sensor.

Figure 5:
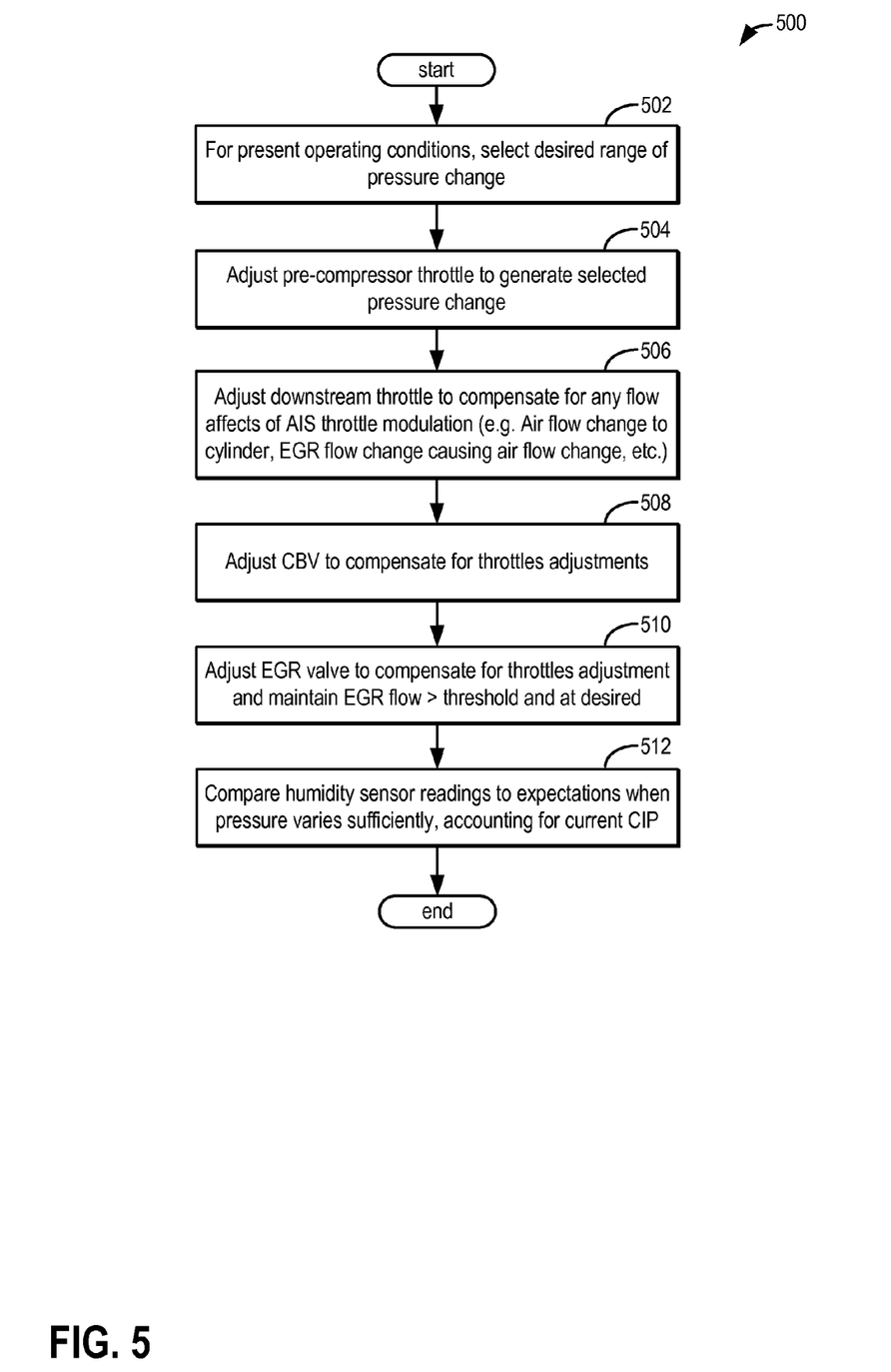
FIG. 5 shows a flow chart of a method for running an intrusive diagnostic test for high specific and relative humidity conditions
Figure 6:
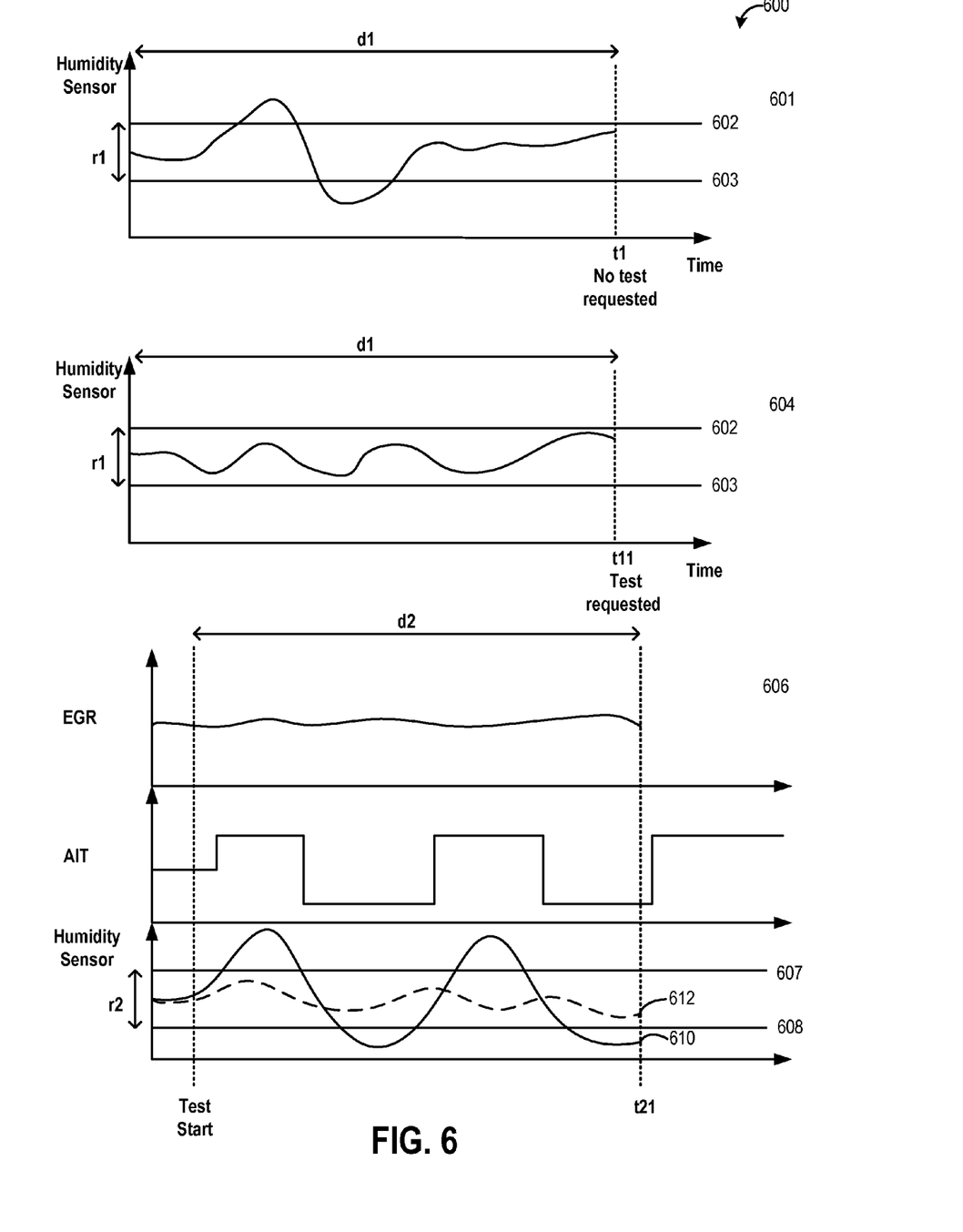
FIG. 6 shows a graphical example of humidity sensor readings for an intrusive diagnostic test based on absolute humidity

Based on the determination of the intrusive diagnostic, such as the routine of FIG. 5, at 314, an indication of degradation (or lack thereof) is reported by generating a stored diagnostic message and implementing default action in response to the indication. Default actions in response to sensor degradation include setting measured humidity to a lower, or minimum, threshold value to enable conservative EGR and spark settings during subsequent engine operation until sensor degradation has been rectified. Another example may include adjusting spark timing, fuel injection, and boost control to be responsive to the lower threshold value but independent of the humidity sensor reading.

Returning to 308, if the ambient air does not have high specific and relative humidity (e.g. the ambient air is cold and dry) then it may be that the ambient air has low specific and relative humidity. In one example, changes in relative humidity may be observed when ambient conditions have low specific and relative humidity with increased temperatures. Regardless of humidity, increasing the air temperature near the humidity sensor may cause a change in the temperature reading by temperature sensor 206 (shown in FIG. 2). At 402, it is determined if a cold start needs to be performed. Following a cold-start, at 408, a passive test is performed. In one embodiment, from a cold-start, under-hood temperatures can rise over ambient temperatures; thus, increasing temperature change while holding the specific humidity constant. Therefore, at 410, it is determined if the temperature sensor readings varied greater than the threshold T1 over previous operating conditions. For example, the routine can compare a current reading at the current operating conditions to previous readings at previous operating conditions to identify whether over a duration, a rise in temperature greater than ambient conditions. Thus, under-hood temperatures should rise over ambient conditions thereby causing a change in relative humidity. If the humidity readings do not vary, degradation of the temperature sensor is possible; therefore, an intrusive diagnostic test is run at 404 (see also FIG. 7). However, at 410, if the humidity sensor readings vary greater than the threshold (T1), then the intrusive diagnostic test (412) and a humidity sensor diagnostic test (414) are not run.

Returning to 402, if the engine does not undergo a cold start, at 404, an intrusive adjustment of engine operation may be performed in order to improve observability of temperature sensor performance and thus enable temperature sensor diagnostics. In one example, the intrusive adjustment may include a forced rise in temperature near the temperature-based humidity sensor. Specifically, a rise in temperature may be adjusted using heater 202 of humidity sensor 94. The degree of temperature change of heater 202 may be selected based on current operating conditions. For example, by adjusting the heater of the humidity sensor across a range of temperatures, during engine operation conditions (e.g. engine idle), the humidity sensor may be sensitive to the variations in relative humidity, and thus variation in the humidity sensor reading that correlates with the temperature change may be used to determine proper sensor functionality. In one embodiment, the temperature increase causes an increase in relative humidity when the specific humidity remains constant.

Figure 7:
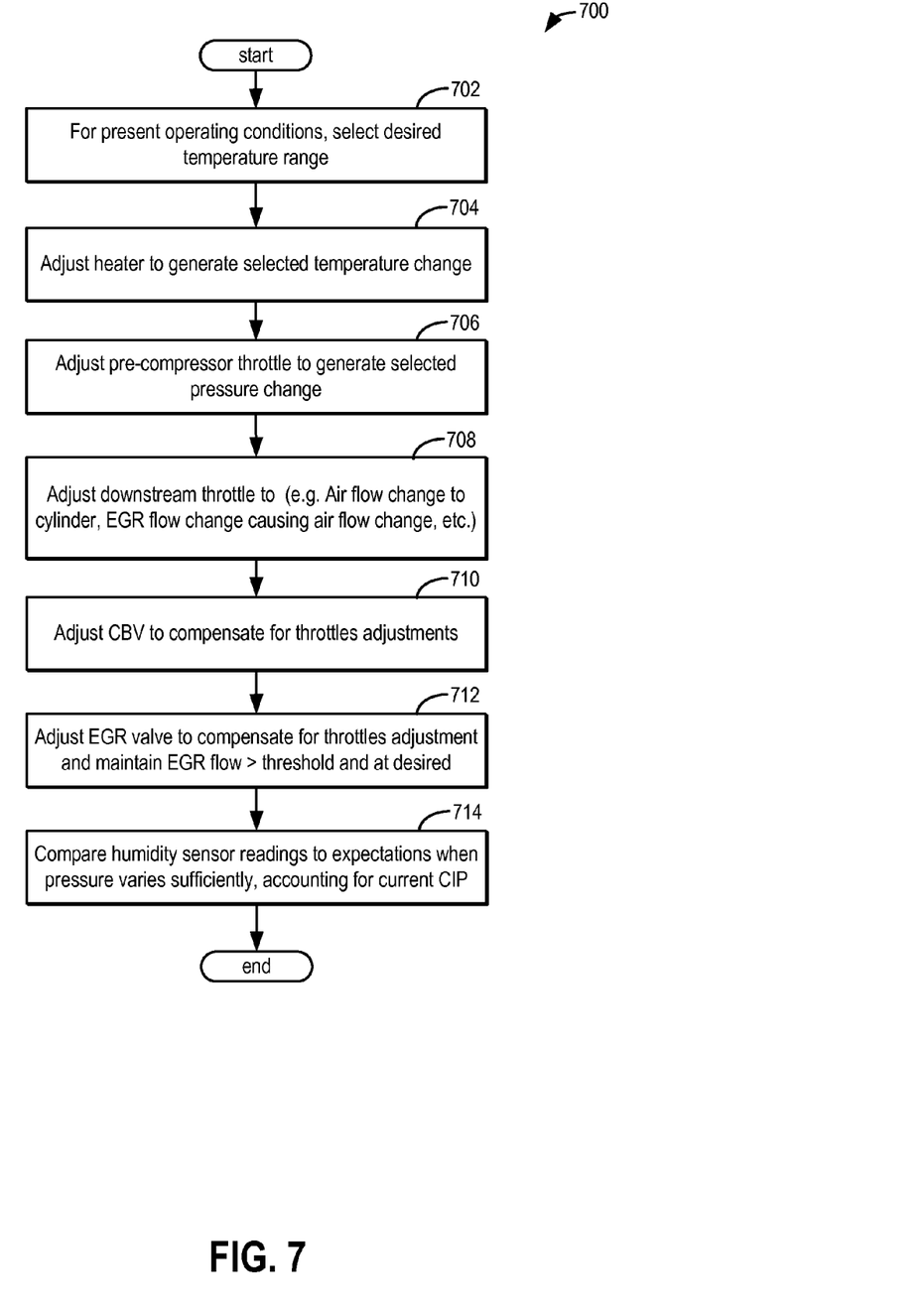
FIG. 7 shows a flow chart of a method for running an intrusive diagnostic test for low specific and relative humidity conditions
Figure 8:
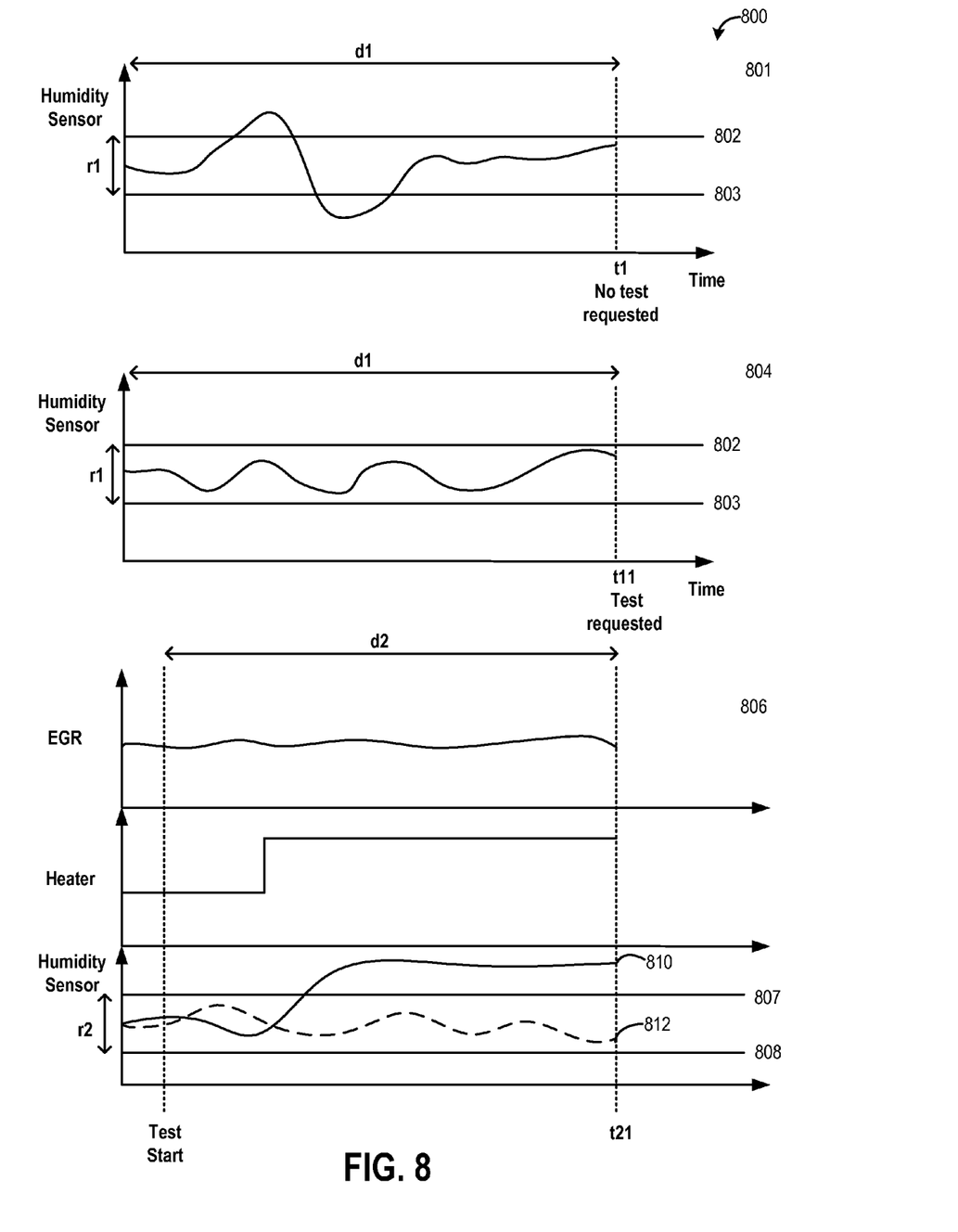
FIG. 8 shows a graphical example of humidity sensor readings for an intrusive diagnostic test based on temperature

Based on the determination of the intrusive diagnostic, such as the routine of FIG. 7, at 406, an indication of degradation (or lack thereof) is reported by generating a stored diagnostic message and implementing default action in response to the indication.

Additional details of an example method for running an intrusive diagnostic test for a humidity sensor are presented at FIG. 5. Method 500 begins at 502 by varying pressure at the humidity sensor at present operating conditions. For example, during engine operation, gasses are flowing into a turbocharger boosting engine intake air downstream of a humidity sensor and upstream of a compressor, as explained with regard to FIG. 1. For example, the flowing gases may include low-pressure EGR and crankcase gasses flowing at a flow level greater than a non-zero threshold. The routine continues on to 504 where the pre-compressor throttle, located upstream from the compressor, is adjusted to generate varying pressure change. At 506, the throttle downstream of the compressor is adjusted to compensate for any flow affects from the upstream pre-compressor throttle adjustment. In order to do this, the downstream throttle adjustment is selected based on the degree of upstream throttle adjustment responsiveness to boost level. For example, higher boost levels enable larger adjustment of upstream throttle since the airflow effect at the engine cylinders can be more easily compensated by the downstream throttle, for example when the boost level is higher than an ambient pressure level.

In addition, adjusting both the throttles upstream and downstream of the compressor may result in inadvertent compressor surge. Therefore, the compressor bypass valve at 508 and the EGR valve at 510 may be adjusted in response to the adjustments of both downstream and upstream throttles. In addition, at 510, adjustment of the EGR valve allows an EGR flow threshold to be maintained. At 512, when the threshold increases sufficiently with the increasing boost levels, the humidity sensor readings can be compared to the expected values.

In one example, the pre-compressor throttle may be modulated about an average value based on driver requested engine torque and vehicle speed conditions. The degree of modulation may be based on the boost level, as described herein. Concurrently, the downstream throttle may be modulated to counteract airflow disturbances into the intake manifold caused by the pre-compressor throttle modulation. Also concurrently, LP-EGR and/or HP-EGR valves may be adjusted to maintain EGR flows at desired levels and compensate for the downstream pressure variations caused by movement of the pre-compressor throttle and/or downstream throttle. At the same time, compressor surge may be monitored and if surge conditions are generated by the modulation for humidity sensor diagnostics, the CBV may be adjusted. Additional examples of operation are described with regard to FIG. 6.

Additionally, the multiple throttles in the air induction system may be adjusted in coordination during the intrusive diagnostic test to maintain flow into the engine, and thus engine torque, at a desired value. In this regard, the throttle 44 is adjusted responsive to a desired and actual cylinder or engine airflow, or manifold pressure, and the compressor inlet pressure and humidity sensor pressure may be adjusted via adjustments of the pre-compressor throttle. In this way, the throttle 44 can counteract flow effects created by adjustment of the pre-compressor throttle 55.

Now turning to FIG. 6, graph 600 shows example humidity sensor readings over time for selected operating conditions. Plot 601 shows a humidity range (r1) with an upper threshold 602 and lower threshold 603. When the engine is operating and the entry conditions are present, over a duration of time (d1), the humidity sensor readings may passively vary greater than threshold and no intrusive test is carried out. In another example, plot 604 shows conditions where the engine is operating and the entry conditions are present, over duration of time (d1), the humidity sensor readings are not varying sufficiently. Therefore an intrusive diagnostic test is needed (see plot 606). For the example intrusive diagnostic test illustrated at 606, EGR remains substantially constant, such as constant within 5% of an average EGR flow rate due to the compensation described herein. However, the pre-compressor throttle is adjusted to continually increase and decrease over the full duration (d2). The humidity sensor range has an upper threshold 607 and lower threshold 608. At the start of the test, the humidity sensor reading increases when pre-compressor throttle opens and decreases when pre-compressor throttle closes (610) over a duration of time (d2); therefore, indicating a lack of degradation in the humidity sensor. If the humidity sensor reading stays within the threshold during the increased opening and decreased opening of pre-compressor throttle, (e.g., insufficient change in the humidity sensor reading (612), then the readings indicate there is degradation of the humidity sensor. Further, humidity sensor readings at 612 also indicate a change in frequency of the variation, which is also indicative of sensor degradation in addition to, or in place of, the readings being within the threshold values.

Additional details of an example method for running an intrusive diagnostic test for a temperature sensor are presented at FIG. 7. Method 700 begins at 702 by increasing the temperature at the humidity sensor at present operating conditions. For example, during engine operation (e.g. engine idle), underhood temperatures can rise over ambient temperatures thus changing relative humidity with increasing temperatures, as explained with regard to FIG. 1. At 704, the heater is adjusted to generate heat based on a selected temperature range. The routine continues on to 706 where the pre-compressor throttle, located upstream from the compressor, is adjusted to generate a constant pressure within a set range. At 708, the throttle downstream of the compressor is adjusted to compensate for any flow affects from the upstream pre-compressor throttle adjustment. In order to do this, the downstream throttle adjustment is made based on the degree of upstream throttle adjustment responsiveness to boost level. For example, higher boost levels enable larger adjustment of upstream throttle since the airflow effect at the engine cylinders can be more easily compensated by the downstream throttle, for example when the boost level is higher than an ambient pressure level. In addition, adjusting both the throttles upstream and downstream of the compressor may result in inadvertent compressor surge.

Therefore, the compressor bypass valve at 710 and the EGR valve at 712 may be adjusted in response to the adjustments of both downstream and upstream throttles. In addition, at 712, adjustment of the EGR valve allows an EGR flow threshold to be maintained. At 714, when the threshold increases sufficiently with increasing temperature, the humidity sensor readings can be compared to the expected values.

Now turning to FIG. 8, graph 800 shows example temperature sensor readings over time for selected operating conditions. Plot 801 shows a temperature range (r1) with an upper threshold 802 and lower threshold 803. When the engine is operating and the entry conditions are present, over a duration of time (d1), the temperature sensor readings may passively vary greater than threshold and no intrusive test is carried out. In another example, plot 804 shows conditions where the engine is operating and the entry conditions are present, over duration of time (d1), the temperature sensor readings are not varying sufficiently. Therefore an intrusive diagnostic test is needed (see plot 806). For the example intrusive diagnostic test illustrated at 806, EGR remains substantially constant, such as constant within 5% of an average EGR flow rate due to the compensation described herein. However, the heater is adjusted to a specific temperature over the full duration (d2). The humidity sensor range has an upper threshold 807 and lower threshold 808. At the start of the test, the humidity sensor reading increases when the temperature increases (810) over a duration of time (d2); therefore, indicating a lack of degradation in the humidity sensor. If the humidity sensor reading stays within the threshold during the increase in temperature, (e.g., insufficient changes in the humidity sensor reading (812), then the readings indicate there is degradation of the temperature sensor.

In this way, the example methods described herein include flowing gasses into an engine intake air downstream of a humidity sensor and upstream of a compressor, and indicating humidity sensor degradation when humidity readings of the sensor change by less than a first threshold while pressure at the sensor changes greater than a second threshold.

Note that the example control and estimation routines included herein can be used with various system configurations. The specific routines described herein may represent one or more of any number of processing strategies such as event-driven, interrupt-driven, multi-tasking, multi-threading, and the like. As such, various actions, operations, or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, functions, or operations may be repeatedly performed depending on the particular strategy being used. Further, the described operations, functions, and/or acts may graphically represent code to be programmed into computer readable storage medium in the control system Further still, it should be understood that the systems and methods described herein are exemplary in nature, and that these specific embodiments or examples are not to be considered in a limiting sense, because numerous variations are contemplated. Accordingly, the present disclosure includes all novel and non-obvious combinations of the various systems and methods disclosed herein, as well as any and all equivalents thereof.

The invention claimed is:

1. An engine method comprising,
    while flowing gasses into an engine intake air downstream of a humidity sensor and upstream of a compressor, indicating humidity sensor degradation when relative humidity readings increase by less than a first threshold while air temperature at the humidity sensor increases greater than a second threshold.

2. The method of claim 1, wherein flowing gasses includes flowing low-pressure EGR.

3. The method of claim 1, wherein flowing gasses includes flowing low-pressure EGR and crankcase gasses.

4. The method of claim 1, further comprising flowing crankcase gasses into the engine intake air upstream of the humidity sensor.

5. The method of claim 1, wherein relative and specific humidity are lower than a third threshold.

6. The method of claim 1, wherein the humidity sensor is a temperature-based humidity sensor.

7. The method of claim 6, further comprising generating an air temperature change during a cold engine start.

8. The method of claim 7, wherein an increase in underhood temperature generates an increase in intake air temperature from below to above ambient air.

9. The method of claim 6, further comprising generating an air temperature change by adjusting a heater contained in the humidity sensor, the heater being located upstream of a capacitance sensor contained in the humidity sensor.

10. The method of claim 9, wherein the heater adjustment generates an increase in air temperature greater than a threshold, the air temperature being measured by an air temperature sensor contained in the humidity sensor and located downstream of the capacitance sensor.

11. The method of claim 10, wherein indicating degradation includes setting a diagnostic code and generating a diagnostic message, and wherein the heater is spaced away from the capacitance sensor.

12. The method of claim 11, further comprising implementing default action in response to the indication, the default action including setting measured relative humidity to a lower threshold value, and adjusting spark timing, fuel injection, and boost control responsive to the lower threshold value independent of the humidity sensor reading.

13. A diagnostic method for a humidity sensor, comprising:
    generating an indication of humidity from the humidity sensor while varying air temperature at the sensor, the humidity sensor positioned upstream of a compressor in an engine intake system; and indicating degradation of the humidity sensor when the indication of humidity changes by less than a threshold amount with the variation in air temperature;
    where the humidity sensor comprises a capacitance sensor and a heater, the heater positioned upstream of the capacitance sensor.

14. The method of claim 13, wherein the compressor is coupled in a turbocharger boosting engine intake air, wherein the engine intake system includes an upstream throttle located in the intake system upstream of the compressor and a downstream throttle located in the intake system downstream of the compressor.

15. The method of claim 14, further comprising adjusting engine operation in response to the indication, and wherein the indicating includes setting a diagnostic code stored in memory.

16. The method of claim 15, wherein the humidity sensor includes a temperature sensor located downstream of the capacitance sensor, and the humidity sensor indicates relative humidity.

17. The method of claim 15, further comprising adjusting the heater in the humidity sensor to generate the variation in air temperature, the variation in air temperature being generated upstream of the capacitance sensor.

18. A system, comprising:
    an engine having an intake system with a compressor therein;
    a first throttle positioned in an intake upstream of the compressor;
    a second throttle positioned in the intake downstream of the compressor;
    a humidity sensor positioned in the intake between the first throttle and the compressor, the humidity sensor comprising a heater, a pair of capacitive plates, and a temperature sensor, the heater being located upstream of the capacitive plates; and
    a controller with memory having non-transitory instructions therein, including instructions to indicate humidity sensor degradation when relative humidity readings of the humidity sensor increase by less than a first threshold while air temperature at the temperature sensor increases greater than a second threshold.

19. The method of claim 14, further comprising adjusting the upstream throttle and the downstream throttle while the variation in air temperature is generated.

20. The system of claim 18, wherein the heater is spaced away upstream from the pair of capacitive plates.

* * * * *